United States Patent [19]

Neuzil et al.

[11] 3,969,422
[45] July 13, 1976

[54] PROCESS FOR THE SEPARATION OF CRESOL ISOMERS

[75] Inventors: Richard W. Neuzil, Downers Grove; Donald H. Rosback, Elmhurst, both of Ill.

[73] Assignee: Universal Oil Products Company, Des Plaines, Ill.

[22] Filed: Feb. 19, 1975

[21] Appl. No.: 551,456

Related U.S. Application Data

[63] Continuation-in-part of Ser. No. 367,685, June 6, 1973, abandoned.

[52] U.S. Cl. .................. 260/621 B; 260/627 G; 260/624 A
[51] Int. Cl.² ................ C07C 39/06; C07C 37/24
[58] Field of Search ........ 260/621 A, 621 B, 624 A, 260/627 G

[56] References Cited
UNITED STATES PATENTS

| | | | |
|---|---|---|---|
| 2,789,143 | 4/1957 | Fleck | 260/621 B |
| 3,014,078 | 12/1961 | Arnold et al. | 260/621 B |
| 3,179,703 | 4/1965 | Rieman et al. | 260/624 A |

Primary Examiner—James O. Thomas, Jr.
Assistant Examiner—W. B. Lone
Attorney, Agent, or Firm—James R. Hoatson, Jr.; Thomas K. McBride; William H. Page, II

[57] ABSTRACT

An improved process for the separation of a para-cresol from a feed mixture containing para-cresol and at least one other cresol isomer which process employs a crystalline aluminosilicate adsorbent to selectively adsorb para-cresol from the feed mixture. The improvement basically comprises employing a desorbent material comprising an alcohol to increase the selectivity of the adsorbent for para-cresol thereby allowing a more efficient separation with a higher purity extract stream recovered from the process.

25 Claims, No Drawings

PROCESS FOR THE SEPARATION OF CRESOL ISOMERS

CROSS-REFERENCE TO RELATED APPLICATIONS

This application is a continuation-in-part application of our prior copending application Ser. No. 367,685 which was filed on June 6, 1973, and now abandoned, all the teachings of which are incorporated herein by specific reference thereto.

BACKGROUND OF THE INVENTION

1. Field of the Invention

The field of art to which the claims invention pertains is solid-bed adsorptive separation with an adsorbent comprising a zeolite. More specifically, the claimed invention relates to an improved process for the separation of cresol isomers by employing a solid crystalline aluminosilicate adsorbent which selectively removes para-cresol from the feed mixture. The para-cresol is then recovered from the adsorbent through a desorption step which employs a desorbent material containing an alcohol.

2. Description of the Prior Art

It is known in the separation art that certain crystalline aluminosilicates can be used to separate hydrocarbon species from mixtures thereof. In particular, the separation of normal paraffins from branched chained paraffins can be accomplished by using the type A zeolites which have pore openings from 3 to about 5 Angstroms. Such a separation process is disclosed for example in U.S. Pat. Nos. 2,986,589 and 3,201,491. These adsorbents allow a separation based on the physical size differences in the molecules by allowing the smaller or normal hydrocarbons to be passed into the cavities within the crystalline aluminosilicate adsorbent, while excluding the larger or branched chain molecules.

U.S. Pat. Nos. 3,265,750 and 3,510,423 for example disclose processes in which larger pore diameter zeolites such as the type X or type Y structured zeolites can be used to separate olefinic hydrocarbons.

The type X or type Y zeolites have additionally been employed in processes to separate individual hydrocarbon isomers. In the process described in U.S. Pat. Nos. 3,558,730; 3,558,732; 3,626,020; and 3,686,342, for example, they are used to separate desired xylene isomers; in U.S. Pat. No. 3,668,267 they are used to separate particular alkyl substituted naphthalenes.

More specifically, U.S. Pat. No. 3,014,078 teaches the separation of cresol isomers by employing an adsorbent consisting of a crystalline zeolitic metallo aluminosilicate to selectively adsorb a cresol isomer from a feed mixture thereby producing a rich adsorbent. In the preferred mode of operation, the adsorbed isomer is then removed by contacting with a displacement exchange fluid. A preferred displacement exchange fluid is phenol although other materials which may be employed include ethers, aromatic hydrocarbons, and paraffin hydrocarbons.

The present invention relates to an improved process for separating for the separation of cresol isomers. In particular we have found that employing a desorbent material comprising an alcohol to remove the selectively adsorbed para-cresol isomer from the zeolitic adsorbent increases the selectivity of the adsorbent for para-cresol with respect to the other cresol isomers thereby permitting a more efficient separation with a higher purity extract stream recovered from the process.

SUMMARY OF THE INVENTION

It is, accordingly, a broad objective of our invention to provide an improved process for the separation of para-cresol from a feed mixture containing para-cresol and at least one other cresol isomer.

In brief summary, our invention is, in one embodiment, an improved process for separating para-cresol from a feed mixture containing para-cresol and at least one other cresol isomer which process comprises: (a) contacting at adsorption conditions said feed mixture with a crystalline aluminosilicate selected from the group consisting of type X structured and type Y structured zeolites containing one or more selected cations at the exchangeable cationic sites thereby selectively adsorbing para-cresol from said feed mixture; and, (b) contacting said adsorbent with a desorbent material at desorption conditions to remove the adsorbed para-cresol therefrom; the improvement which comprises employing a desorbent material comprising an alcohol which is soluble in the feed mixture at adsorption and desorption conditions and which has an average boiling point substantially different than that of the feed mixture.

Other embodiments and objects of the present invention encompass details about feed mixtures, adsorbents, desorbent materials, and operating conditions all of which are hereinafter disclosed in the following discussion of each of these facets of the present invention.

The process of this invention provides an improved alternative to the separation of para-cresol from mixed cresols than by toluene sulfonation and caustic fusion. Para-cresol finds specific use, for example, as a starting material in a manufacture of butylated hydroxy toluene, a widely-used antioxidant.

DESCRIPTION OF THE INVENTION

Preferred adsorbents which can be used in the adsorptive separation of cresols are certain crystalline aluminosilicates or molecular sieves including both the natural and synthetic aluminosilicates. Such crystalline aluminosilicates have cage structures in which the alumina and silica tetrahedra are intimately connected in an open three dimensional network. The tetrahedra are cross-linked by the sharing of oxygen atoms with spaces between the tetrahedra occupied by water molecules prior to partial or total dehydration of this zeolite. The dehydration of the zeolite results in crystals interlaced with cells having molecular dimensions. Thus, the crystalline aluminosilicates are often referred to as molecular sieves and separations performed with molecular sieves are generally thought to take place by a physical "sieving" of smaller from larger molecules appearing in the feed mixture. In the separation of cresol isomers, however, the separation of the isomers apparently occurs because of differences in electrochemical attraction of the different isomers and the adsorbent rather than on pure physical size differences in the isomer molecules.

In hydrated form, the preferred crystalline aluminosilicates generally encompass those zeolites represented by the formula 1 below:

Formula 1

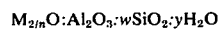

where M is a cation which balances the electrovalence of the tetrahedra and is generally referred to as an exchangeable cationic site, $n$ represents the valence of the cation, $w$ represents the moles of $SiO_2$, and $y$ represents the moles of water. The cations may be any one of a number of cations which will hereinafter be described in detail.

Adsorbents comprising the type X structured and type Y structured zeolites are especially preferred for the adsorptive separation of the cresol isomers. These zeolites are described and defined in U.S. Pat. Nos. 2,882,244 and 3,120,007 respectively. The terms "type X structured" and "type Y structured" zeolites as used herein shall include all zeolites which have a general structure as represented in the above two cited patents and additionally shall specifically include crystalline aluminosilicates produced from either of the zeolites described in the two patents as starting materials by various ion-exchange techniques or thermal treatments or combinations thereof.

The type X structured zeolites can be represented in terms of mole oxides as represented in formula 2 below:

Formula 2

$$(0.9 \pm 0.2)M_{2/n}O:Al_2O_3:(2.5 \pm 0.5)SiO_2 \cdot yH_2O$$

where M represents at least one cation having a valence of not more than 3, $n$ represents the valence of M and $y$ is a value up to about 9 depending upon the identity of M and the degree of hydration of the crystalline structure.

The type Y structured zeolites can be represented in terms of the mole oxides for the sodium form as represented by formula 3 below:

Formula 3

$$(0.9 \pm 0.2)Na_2O:Al_2O_3 \cdot wSiO_2 \cdot yH_2O$$

where $w$ is a value of greater than about 3 up to 8, and $y$ may be any value up to about 9.

Adsorbents contemplated herein include not only the sodium form of the type X and the type Y zeolites but also crystalline materials obtained from such zeolites by partial or complete replacement of the sodium at the exchangeable cationic sites with one or more other specified cations. The term "exchangeable cationic sites" generally refers to the sites occupied by sodium cations present in the type X and type Y zeolites as indicated in Formula 2 and Formula 3 above. Most of the sodium cations originally present at these sites can be replaced or exchanged with other cations.

Cationic or base exchange methods are generally known to those familiar with the field of crystalline aluminosilicate production. They are generally performed by contacting the zeolite with an aqueous solution of the soluble salts of the cation or cations desired to be placed upon the zeolite. The desired degree of exchange takes place and then the sieves are removed from the aqueous solution, washed and dried to a desired water content. It is contemplated that cation exchange operations may take place using individual solutions of desired cations to be placed on the zeolite or using an exchange solution containing a mixture of cations, where two or more desired cations are to be placed on the zeolite.

The cations which may be placed upon the zeolite include cations selected from, but not limited to, the Group IA, Group IIA, and Group IB metals of the Periodic Table of Elements. Specific cations which show a preferential selectivity for para-cresol with respect to other cresol isomers include lithium, sodium, potassium, rubidium, cesium, beryllium, magnesium, calcium, strontium, barium, silver, manganese, cadmium, and copper. Where the above cations are used, para-cresol would be the preferentially adsorbed component of the feed mixture. In the process of this invention we have found that an adsorbent comprising a type X or type Y zeolite containing barium or potassium as a selected single cation at the exchangeable cationic sites is particularly preferred.

Type X or Type Y zeolites containing the following combinations of cations have also been shown to be suitable for para-cresol separation. These cations include potassium and barium, potassium and beryllium, potassium and manganese, rubidium and barium, cesium and barium, copper and cadmium, copper and silver, zinc and silver, and copper and potassium, with the barium and potassium combination being preferred. A particularly preferred adsorbent is one comprising type X or type Y zeolite containing barium and potassium at the exchangeable cationic site, in a weight ratio of barium to potassium of from about 1 to about 100.

When singular cations are based exchanged upon a zeolite the singular cations can comprise anywhere from 5 to 75 wt. % on a relative volatile free basis of the zeolite depending upon the molecular weight of the material exchanged upon the zeolite. It is contemplated that when single ions are placed upon the zeolite that they may be on the zeolite in concentrations of from about 1% to about 100% of the original cations present (generally sodium) upon the zeolite prior to its being ion-exchanged. By knowing the empirical formula of the zeolite used, its water content and the percentage of any amorphous material or binder present if any it is possible to calculate the percentage of ion exchange that has taken place.

When two or more cations are placed upon the zeolite there are two parameters in which one can operate in order to effectively produce a zeolite having the maximum selective properties. One of the parameters is the extent of the zeolite ion exchange which is determined by variables such as the length of ion-exchange times, ion-exchange temperature, and cation concentration. The other parameter is the ratio of individual cations placed on the zeolite. In instances in which the cation pairs comprise a Group IIA metal and a Group IA metal the weight ratio of these two components upon the zeolite can vary anywhere from about less than one up to about one hundred depending upon the molecular weight of the Group IIA or Group IA metal.

In the process of this invention we have additionally found that a small amount of water on the adsorbent is beneficial to promote relatively sharp isomer separation and to prevent "tailing" of one cresol isomer into another. The preferred range of water on the adsorbent is from about 3 to about 8 wt. % LOI at 600°C. This desired range can be maintained by intermittent or preferably continuous water addition to the process. In this specification, the volatile matter content (generally water) of the zeolitic adsorbent is determined by first weighing the adsorbent and thereafter contacting the adsorbent in a high temperature furnace from 600° C.

to 900° C. under an inert purge gas stream such as nitrogen for a period of time sufficient to achieve a constant weight. The sample is then cooled under an inert atmosphere and weighed to determine the difference in weight between the adsorbent before it was passed into the oven and afterwards. The difference in weight is calculated as a loss on ignition (LOI) and represents the volatile matter present within the adsorbent. The chemical analyses of the zeolites are generally reported on a volatile-free basis by correcting the as-received analyses for the volatile content of the sample.

The ortho-, meta-, and para-cresols are commonly obtained by the distillation of coal tar. An unpurified mixture of the three isomeric cresols in known as "tricresol" or "cresylic acid". Since the amounts obtainable by this source may not equal the demand, they can also be produced from the toluidines by the diazo reaction or more frequently by toluene sulfation and caustic fusion. Proper selection of reaction conditions favors the production of para-cresol. Since the boiling points for ortho-, meta-, and para-cresol are respectively 191.5° C., 202.8° C., and 202.5° C., it can be seen that ortho-cresol can be recovered by fractionation but because of their close boiling points meta- and para-cresols cannot. The separation of meta- and para-cresol thus is ideally suited to separation by selective adsorption with a solid adsorbent.

We have found that the selectivity of adsorbents comprising type X and type Y zeolites for para-cresol with respect to the other cresol isomers is strongest when the feed mixture to be separated contains concentrations of para-cresol and one or more other cresol isomers of up to about 15 vol. % each. Apparently because of the relatively high acidity of cresols, selectivity of the adsorbent for any cresol isomer diminishes as the cresol concentration in the feed mixture increases. Separation of a desired isomer by selective adsorption takes place, it is theorized, because of a rather delicate acidity/basicity difference between the desired isomer and the adsorbent. At cresol isomer concentrations higher than about 15 vol. % each of para-cresol and at least one other cresol isomer this difference diminishes. The feed mixtures may contain as diluents materials which are generally less selectively adsorbed (if at all) in this adsorption system than any of the cresol isomers and in which the cresols are soluble. As one example, hereinafter described liquid desorbent materials can be employed as diluents to achieve the proper concentrations of cresol isomers in the feed mixture.

To separate para-cresol from a feed mixture containing para-cresol and at least one other cresol isomer the mixture is contacted with an adsorbent comprising a crystalline aluminosilicate and the para-cresol is more selectively adsorbed and retained by the adsorbent while the other cresol isomers are relatively unadsorbed and are removed from the interstitial void spaces between the particles of adsorbent and the surface of the adsorbent. The adsorbent containing the more selectively adsorbed para-cresol is referred as a "rich" adsorbent--rich in the more selectively adsorbed para-cresol.

The more selectively adsorbed feed component is commonly referred to as the extract component of the feed mixture, while the less selectively adsorbed component is referred to as the raffinate component. Fluid streams leaving the adsorbent comprising an extract component and comprising a raffinate component are referred to, respectively, as the extract stream and the raffinate stream. Thus, the raffinate stream will contain as raffinate components all of the feed mixture isomers except para-cresol and the extract stream will contain para-cresol as the extract component.

Although it is possible by the process of this invention to produce high purity (98% or greater), para-cresol at high recoveries, it will be appreciated that an extract component is never completely adsorbed by the adsorbent, nor is a raffinate component completely non-adsorbed by the adsorbent. Therefore, small amounts of a raffinate component can appear in the extract stream, and, likewise, small amounts of an extract component can appear in the raffinate stream. The extract and raffinate streams then are further distinguished from each other and from the feed mixture by the ratio of the concentrations of an extract component and a specific raffinate component, both appearing in the particular stream. For example, the ratio of concentration of the more selectively adsorbed para-cresol to the concentration of less selectively adsorbed meta-cresol will be highest in the extract stream, next highest in the feed mixture, and lowest in the raffinate stream. Likewise, the ratio of the less selectively adsorbed metacresol to the more selectively adsorbed para-cresol will be highest in the raffinate stream, next highest in the feed mixture, and the lowest in the extract stream.

The adsorbent can be contained in one or more chambers where through programmed flow into and out of the chambers separation of para-cresol is effected. The adsorbent will preferably be contacted with a desorbent material which is capable of displacing the adsorbed para-cresol from the adsorbent. An extract stream comprising para-cresol and desorbent material will then be withdrawn from the adsorbent and the desorbent material separated thereby leaving high purity para-cresol. Alternatively, the para-cresol could be removed from the adsorbent by purging or by increasing the temperature of the adsorbent or by decreasing the pressure of the chamber or vessel containing the adsorbent or by a combination of these means.

The adsorbent may be employed in the form of a dense compact fixed bed which is alternatively contacted with the feed mixture and a desorbent material (hereinafter described in more detail). In the simplest embodiment of the invention the adsorbent is employed in the form of a single static bed in which case the process is only semi-continuous. A set of two or more static beds may be employed in fixed-bed contacting with appropriate valving so that the feed mixture is passed through one or more adsorbent beds while the desorbent material is passed through one or more of the other beds in the set. The flow of feed mixture and desorbent material may be either up or down through the desorbent. Any of the conventional apparatus employed in static bed fluid-solid contacting may be used. Countercurrent moving-bed or simulated countercurrent moving-bed liquid flow systems, however, have a much greater separation efficiency than fixed adsorbent bed systems and are therefore preferred. In the moving-bed or simulated moving-bed processes the adsorption and desorption operations are continuously taking place which allows both continuous production of an extract and a raffinate stream and the continual use of feed and desorbent streams. One preferred processing flow scheme which can be utilized to effect the process of this invention includes what is known in the art as the simulated moving-bed countercurrent system. The general operating sequence of such a flow system is described in U.S. Pat. No. 2,985,589 issued to D. B. Broughton. This patent generally described the processing sequence involved in a particular simulated moving-bed countercurrent solid-fluid contacting process. The processing sequence generally described in that patent is the preferred mode of operating the separation process disclosed herein.

One broad embodiment of this process is a process for separating para-cresol from a feed mixture comprising para-cresol and at least one other cresol isomer which process generally employs the operating sequence described in U.s. Pat. No. 2,985,589 and which comprises the steps of: contacting the feed at adsorption conditions with a particular zeolitic adsorbent thereby selectively adsorbing para-cresol; withdrawing from the adsorbent bed a stream comprising less selectively adsorbed components in the feed; contacting the adsorbent at desorption conditions with a desorbent material to effect the removal of para-cresol from the adsorbent; and, withdrawing from the adsorbent a stream comprising desorbent material and para-cresol.

Adsorption and desorption conditions for adsorptive separation processes can generally be either in the liquid or vapor phase or both but for cresol separation processes employing zeolitic adsorbents all liquid-phase operations are preferred because of the lower temperature requirements and the slightly improved selectivities associated with the lower temperatures. Adsorption conditions will include temperature within he range of from about 100° F. up to about 500° F. and will include pressures in the range from about atmospheric to about 500 psig. Pressures higher than about 500 psig. do not appear to affect the selectivity to a measureable amount and additionally would increase the cost of the process. Desorption conditions for the process of the invention shall generally include the same range of temperatures and pressures as described for adsorption operations. The desorption of the selectively adsorbed isomer could also be effected at subatmospheric pressures or elevated temperatures or both or by vacuum purging of the adsorbent to remove the adsorbed isomer but this process is not directed to these desorption methods.

The desorbent materials which can be used in the various processing schemes employing this adsorbent will vary depending on the type of operation employed. The term "desorbent material" as used herein shall mean any fluid substance capable of removing a selectively adsorbed feed component from the adsorbent. In the swing-bed system in which the selectively adsorbed feed component is removed from the adsorbent by a purge stream, desorbent materials comprising gaseous hydrocarbons such as methane, ethane, etc., or other types of gases such as nitrogen or hydrogen may be used at elevated temperatures or reduced pressure or both to effectively purge the adsorbed feed component from the adsorbent.

However, in processes which are generally operated at substantially constant pressures and temperatures to insure liquid phase, the desorbent material relied upon must be judiciously selected in order that it may displace the adsorbed feed component from the adsorbent with reasonable mass flow rates without itself being so strongly adsorbed as to unduly prevent the extract component from displacing the desorbent material in a following adsorption cycle.

Desorbent materials which can be used in the process of this invention should additionally be substances which are easily separable from the feed mixture that is passed into the process. In desorbing the preferentially adsorbed component of the feed, both desorbent material and the extract component are removed in admixture from the adsorbent. Without a method of separation such as distillation of these two materials, the purity of the extract component of the feed stock would not be very high since it would be diluted with desorbent. It is therefore contemplated that any desorbent material used in this process will have a substantially different average boiling point than that of the feed mixture. The use of a desorbent material having a substantially different average boiling point than that of the feed allows separation of desorbent material from feed components in the extract and raffinate streams by simple fractionation thereby permitting reuse of desorbent material in the process. The term "substantially different" as used herein shall mean that the difference between the average boiling points between the desorbent material and the feed mixture shall be at least about 15° F. The boiling range of the desorbent material may be higher or lower than that of the feed mixture, although for the process of this invention it is preferred that desired desorbent material have a boiling range less than that of the feed material.

The prior art has generally chosen phenol as the preferred "displacement exchange fluid" or desorbent material for separation processes employing an adsorbent comprising crystalline aluminosilicate to separate the cresol isomers. Other materials which have been recognized by the prior art are ethers, aromatic hydrocarbons, and paraffin hydrocarbons. Such desorbent materials are best suited to adsorptive separation processes generally characterized as equilibrium adsorptive type operations. However, in processes characterized by less than equilibrium adsorption, we have discovered that there is a distinct advantage in employing a desorbent material comprising an alcohol and that this advantage results in an improved process for the separation of cresol isomers by selective adsorption on a zeolite-containing adsorbent.

The term "equilibrium adsorption" as used herein shall mean that there is essentially no competitive adsorption of the adsorbent of both desorbent material and an extract component of the feed mixture during the process adsorption step or steps. Equilibrium adsorption essentially takes place in the sequence of steps in which a feed stream which does not contain any desorbent material is first passed through a zeolitic adsorbent bed until the effluent stream which passes out of the adsorbent after contact therewith is essentially of the same composition as the material fed to the adsorbent bed indicating no net transfer of material between the adsorbed material within the adsorbent and the feed stock surrounding the adsorbent. A desorbent material is then passed through the bed of adsorbent to displace the selectively adsorbed components of the feed. In this type sequential operation there is no desorbent material in contact with the adsorbent when adsorption operations are completed (any desorbent initially present on the adsorbent is displaced by feed components).

The term "less than equilibrium adsorption" shall mean that there is this competitive adsorption of desorbent material and an extract component during the process adsorption step. In continuous simulated or actual countercurrent liquid flow systems in which an extract component of the feed is continuously and selectively adsorbed from the feed mixture by a solid adsorbent, there are zones in which there is essentially a simultaneous contacting of the adsorbent during adsorption with a mixture comprising desorbent material and the feed mixture. The presence of feed and desorbent material in admixture creates a condition where there is a competitive adsorption of the adsorbent of both desorbent material and the selectively adsorbed component of the feed mixture.

In most continuous countercurrent solid-fluid separation processes, the solid adsorbent contacts the feed mixture in what is generally referred to as an adsorption zone. The feed and solid adsorbent countercurrently contact each other with the adsorbent passing out of the adsorption zone containing an extract component of the feed and some desorbent within the solid adsorbent. The solid adsorbent is eventually contacted with desorbent material in a desorption zone. The desorbent material displaces an extract component from the solid adsorbent and allows a mixture of desorbent and extract component of the feed to be removed from the process as an extract stream. The extract stream eventually passes to a separation means wherein the desorbent material is separated from the extract component giving a stream enriched in an extract component of the feed. The solid adsorbent after being contacted with the desorbent in the desorption zone, continues to flow in a countercurrent direction in relation to the fluid flow in the system and eventually is recontacted with the feed in the adsorption zone for the adsorption of the extract component of the feed by the solid adsorbent. Between the adsorption zone and desorption zone are located the flushing or rectification zones which by carefully controlled pressure drops and liquid flow rates prevent the raffinate or extract streams from contaminating each other. The material contained in the flushing or rectification zones generally contains desorbent material. The desorbent material in the flushing or rectification zones flushes a raffinate material carried by the solid adsorbent back into the adsorption zone and eventually ends up contacting the adsorbent in the adsorption zone substantially the same time the feed mixture contacts the solid adsorbent in the adsorption zone. The desorbent material which contacts the adsorbent in the adsorption zone causes competitive adsorption between it and the extract component of feed. The presence of desorbent material during the adsorption step can affect selectivity of the adsorbent for the extract component.

We have found that improved separation is obtained in an adsorption process for separating cresol isomers in which the desorbent material is present while adsorption of para-cresol takes place by employing a desorbent material comprising an alcohol. Specifically, we have found that employing such a desorbent material increases the selectivity of particular adsorbents for para-cresol with respect to other cresol isomers and also increases the rate of desorption of para-cresol from the adsorbent. The exact mechanism by which this occurs is not fully understood but it is thought that the alcohols modify the acidity/basicity relationships between the cresol isomers and the adsorbent.

Alcohols which can be used in the process of this invention shall broadly be those which satisfy these two criteria: they shall be soluble in the feed mixture used in the process at adsorption and desorption conditions and they shall have an average boiling point substantially different than that of the feed mixture. The term "substantially different" has been previously defined and means that the difference in the average boiling point shall be at least about 15° F. Preferably the alcohols will be derivatives of normal paraffins or cycloparaffins. Although secondary and tertiary alcohols are suitable for use in the process of our invention, primary alcohols are more preferred because they do not readily dehydrate to form olefins. Even more preferred are those primary alcohols which have boiling points less than, rather than higher than, that of the feed mixture. These particular primary alcohols are preferred because the larger chain higher-boiling primary alcohols tend to behave more like normal paraffins and thus their ability to modify the adsorbent characteristics is diminished. Thus as indicated in Table No. 1 below primary alcohols having from one to and including seven carbon atoms per molecule will be the preferred primary alcohols. Of these 1-hexanol is particularly preferred. Primary alcohols having greater than seven carbon atoms per molecule which generally have boiling points greater than any one of the cresol isomers are not as desirable for use as desorbent materials for this process.

Mixtures of alcohols with hydrocarbons such as paraffins or aromatics are also effective as desorbent materials in the process of this invention. Such hydrocarbons shall be those which are soluble in both the alcohol and the feed mixture at adsorption and desorption conditions and, like the alcohols employed, shall have average boiling points substantially different than that of the feed mixtures. The paraffins can include straight or branched chain paraffins or cycloparaffins which meet these two criteria. Particularly preferred aromatics are benzene, toluene, and the xylenes. Typical concentrations of the alcohol in mixtures of an alcohol and a hydrocarbon can be from a few volume percent up to near 100 vol. % of the total desorbent material mixture but such concentration preferably will be within the range of from about 25 vol. % to about 75 vol. % of the mixture.

Table 1

Normal Boiling Points of Selected Primary Alcohols

|  | normal boiling point, °C |
|---|---|
| Methanol | 64.7 |
| Ethanol | 78.5 |
| 1-Propanol | 97.2 |
| 1-Butanol | 117.7 |
| 1-Pentanol | 138 |
| 1-Hexanol | 157.2 |
| 1-Heptanol | 176 |
| 1-Octanol | 195 |
| 1-Nonanol | 213 |
| 1-Decanol | 231 |
| ortho-cresol | 190.8 |
| para-cresol | 201.1 |
| meta-cresol | 202.8 |
| benzene | 80.1 |
| toluene | 110.6 |
| ortho-xylene | 114.4 |
| meta-xylene | 139.1 |
| para-xylene | 138.3 |

The improvement that results from employing a desorbent material comprising an alcohol can be better understood by brief reference to certain adsorbent properties which are necessary to the successful operation of a selective adsorption process. It will be recognized that improvements in any of these adsorbent characteristics will result in an improved separation process. Among such characteristics are: adsorptive capacity for some volume of an extract component per volume of adsorbent; the selective adsorption of an extract component with respect to a raffinate component and the desorbent material; sufficiently fast rates of adsorption and desorption of the extract component to and from the adsorbent; and, in instances where the components of the feed mixture are very reactive, little or no catalytic activity for undesired reactions such as polymerization and isomerication.

Capacity of the adsorbent for adsorbing a specific volume of an extract component, is of course, a necessity; without such capacity the adsorbent is useless for adsorptive separation. Further, the higher the adsorbent's capacity for an extract component, the better is the adsorbent. Increased capacity of a particular adsorbent makes it possible to reduce the amount of adsorbent needed to separate the extract component contained in a particular charge rate of feed mixture. A reduction in the amount of adsorbent required for a specific adsorptive separation reduces the cost of the separation process. It is important that the good initial capacity of the adsorbent be maintained during actual use in the separation process over some economically desirable life.

The second necessary adsorbent characteristic is the ability of the adsorbent to separate components of the feed; or, in other words, that the adsorbent possess adsorptive selectivity for one component as compared to another component. Some adsorbents demonstrate acceptable capacity but possess little or no selectivity. Silver nitrate on silica gel for instance possesses a large capacity for cresols but little selectivity for one isomer with respect to another. Relative selectivity can be expressed not only for one feed mixture component as compared to another but can also be expressed between any feed mixture component and the desorbent. The relative selectivity, (B), as used throughout this specification is defined as the ratio of two components of an adsorbed phase over the ratio of the same two components in an unadsorbed phase at equilibrium conditions.

Relative selectivity is shown as Equation 1 below:

$$\text{Selectivity} = (B) = \frac{[\text{vol. percent } C/\text{vol. percent } D]_A}{[\text{vol. percent } C/\text{vol. percent } C]_U} \quad \text{Eq. 1}$$

where $C$ and $D$ are two components of the feed represented in volume percent and the subscripts $A$ and $U$ represent the adsorbed and unadsorbed phases respectively. The equilibrium conditions were determined when the feed passing over a bed of adsorbent did not change composition after contacting the bed of adsorbent. In other words, there was no net transfer of material occurring between the unadsorbed and adsorbed phases.

Where selectivity of two components approaches 1.0 there is no preferential adsorption of one component by the adsorbent with respect to the other; they are both adsorbed (or non-adsorbed) to about the same degree with respect to each other. As the (B) becomes less than or greater than 1.0 there is a preferential adsorption by the adsorbent for one component with respect to the other. When comparing the selectivity by the adsorbent of one component C over component D, a (B) larger than 1.0 indicates preferential adsorption of component C within the adsorbent. A (B) less than 1.0 would indicate than component D is preferentially adsorbed leaving an unadsorbed phase richer in component C and an adsorbed phase richer in component D. Desorbent materials ideally would have a selectivity equal to about 1 or slightly less than 1 with respect to an extract component.

Employing a desorbent material comprising an alcohol increases the selectivity of the adsorbent for paracresol with respect to the other cresol isomers thereby permitting sharper separation of the isomers and improving the process.

The third important characteristic is the rate of exchange of the extract component of the feed mixture material or, in other words, the relative rate of desorption of the extract component. This characteristics relates directly to the amount of desorbent material that must be employed in the process to recover the extract component from the adsorbent; faster rates of exchange reduce the amount of desorbent material meeded to remove the extract component and therefore permit a reduction in the operating cost of the process. With faster rates of exchange, less desorbent material has to be pumped through the process and separated from the extract stream for reuse in the process. We have found that the use of a desorbent material comprising an alcohol also increases the transfer rates besides improving the selectivity for para-cresol.

It is also necessary that the adsorbent possess little or no catalytic activity toward any reaction such as polymerization or isomerization of any of the feed components. Such activity might effect adsorbent capacity or selectivity or product yields or all of these, but in the adsorptive separation of cresol isomers with a zeolite-containing adsorbent this is generally not a problem.

In order to test various adsorbent and desorbent materials with a particular feed mixture to measure the adsorbent characteristics of adsorptive capacity and selectivity and exchange rate a dynamic testing apparatus is employed. The apparatus consists of an adsorbent chamber of approximately 70 cc. volume having inlet and outlet portions at opposite ends of the chamber. The chamber is contained within a temperature control means and, in addition, pressure control equipment is used to operate the chamber at a constant predetermined pressure. Chromatographic analysis equipment can be attached to the outlet line of the chamber and used to analyze the effluent stream leaving the adsorbent chamber.

A pulse test, performed using this apparatus and the following general procedure, is used to determine selectivities and other data for various adsorbent systems. The adsorbent is filled to equilibrium with a particular desorbent material by passing the desorbent material through the adsorbent chamber. At a convenient time, a pulse test of feed containing known concentrations of cresol isomers all diluted in desorbent material is injected for a duration of several minutes. For convenience a known concentration of a non-adsorbed tracer compound may be included in the feed. Flow of desorbent material is resumed, and the tracer (if one is employed) and the cresols are eluted as in liquid-solid chromatographic operation. The effluent can be analyzed by on-stream chromatographic equipment and traces of the envelopes of corresponding component peaks developed. Alternatively, effluent samples can be collected periodically and later analyzed separately by gas chromatography.

From information derived from the chromatographic traces adsorbent performance can be rated in terms of capacity index for para-cresol, selectivity for para-cresol with respect to the other cresols and rate of desorption of para-cresol by the desorbent. The capacity index is characterized by the distance between the center of the para-cresol peak envelope and the tracer peak envelope or some other known reference point such as volume of desorbent pumped. It is expressed in terms of the volume in cubic centimers of desorbent pumped during this time interval. Relative selectivity, (B), for para-cresol with respect to the other cresols is characterized by the ratio of the distance between the center of the para-cresol peak envelope and the tracer peak envelope (or other reference point) to the corresponding distances for the other cresol isomers. The rate of exchange of para-cresol with the desorbent can be characterized by the width of the para-cresol peak envelope at half intensity. The narrower the peak width, the faster the desorption rate.

To further evaluate promising adsorbent systems and to translate this type of data into a practical cresol separation process requires actual testing of the best systems in a continuous countercurrent liquid-solid contacting device.

The general operating principles of such a device have been previously described and are found in Broughton U.S. Pat. No. 2,985,589. A specific laboratory-size fluid-solid contacting apparatus utilizing these principles is described in deRosset et al U.S. Pat. No. 3,706,812. The apparatus comprises multiple adsorbent beds with a number of access lines attached to distributors within the beds and terminating at a rotary distributing valve. At a given valve position, feed and desorbent are being introduced through two of the lines and raffinate and extract are withdrawn through two more. All remaining access lines are inactive and when the position of the distributing valve is advanced by one index all active positions will be advanced by one bed. This simulates a condition in which the adsorbent physically moves in a direction countercurrent to the liquid flow. Additional details on adsorbent testing and evaluation techniques may be found in the paper "Separation of $C_8$ Aromatics by Adsorption" by A. J. deRosset, R. W. Neuzil, A. J. Korous, and D. H. Rosback presented at the American Chemical Society, Los Angeles, Calif., Mar. 28–April 2, 1971.

The improved process of this invention for separating para-cresol from a feed mixture containing para-cresol and at least one other cresol isomer, which was demonstrated by pulse tests, was confirmed by actual continuous testing in the apparatus described above.

The examples below illustrate first the selectivity characteristic of adsorbents comprising zeolites which makes possible a process for the adsorptive separation of cresol isomers and second the improvement in that characteristic, as well as in the rate of desorption, which results in the improved process of our invention. The examples are presented to further illustrate the process of the present invention and are not intended to limit the scope and spirit of the invention.

The examples present pulse test results obtained with an adsorbent comprising type X crystalline aluminosilicate which contained barium and potassium cations at the exchangeable cationic sites within the aluminosilicate. Results for one pulse test which employed an adsorbent comprising a type X crystalline aluminosilicate containing calcium cations at the exchangeable cationic sites are also included for comparison. The first-mentioned adsorbent was essentially totally ion-exchanged, contained a weight ratio of barium oxide to potassium oxide of about 3.3, and was approximately 20–40 mesh particle size. Analyses of this adsorbent are shown in Table No. 2 below.

Table 2

| ADSORBENT ANALYSES | |
|---|---|
| Volatile Matter (LOI at 900° C.) | 6.43 |
| $SiO_2$ (volatile free) wt. % | 42.1 |
| $Al_2O_3$ (volatile free) wt. % | 28.3 |
| $Na_2O$ (volatile free) wt. % | 2.0 |
| $K_2O$ (volatile free) wt. % | 6.1 |
| BaO (volatile free) wt. % | 20.3 |
| $SiO_2/Al_2O_3$ | 2.53 |

The latter adsorbent was commercially-available Linde 10X Molecular Sieves of approximately 20–40 mesh particle size.

EXAMPLE I

In this example the adsorbent comprising the type X zeolite containing barium and potassium cations described above was placed in the testing unit and a pulse test was conducted in the following manner.

The desorbent material employed was 15 vol. % phenol in toluene. The feed mixture utilized contained 5 vol. % each of para-cresol and metacresol in desorbent material. Ortho-cresol was omitted from the feed mixture in order to simplify the test and focus on the para/meta selectivity which is the most critical selectivity because of their close boiling points. Additionally from previous experiments it had been determined that the meta- and ortho-isomers behave in substantially the same manner. Since desorbent material was a part of the feed mixture, adsorption of para-cresol took place in the presence of, and in competition with, desorbent material, and; therefore, selectivities were obtained at less than equilibrium conditions. The desorbent was placed in a 70 cc adsorbent column which was maintained at a constant temperature of about 150° C. with constant moderate pressure during the entire operation. A Waters Automatic Fraction Collector was connected to the effluent end of the chamber to sample the effluent every 2.1 minutes.

Desorbent was first pumped through the adsorbent chamber at approximately 1 cc/min at about 150° C. A 4.7 ml feed pulse was then cut into the system via an injection loop and the effluent was periodically sampled in the manner indicated above. A measured void volume of 43.0 cc was used for the 70 cc adsorbent column and sampling was started after 40 cc of desorbent was pumped beginning at feed injection. The individual effluent samples were stoppered after collection and analyzed separately by Gas Chromatography. A digital integrator was used to obtain peak areas and the count produced ($\times 10^{-5}$) was plotted versus cc of desorbent from time of feed injection, for both para- and meta-cresol. This plot produced an envelope for para- and meta-cresols similar to those obtained when using on-stream GC analysis. The cresol samples take 50 minutes to elute from the analytical GC column.

The selectivities were calculated by measuring the cc of the desorbent pumped from the measured 43 cc void volume to the midpoints of the individual para- and meta-cresol envelopes at one-half the peak heights. The ratio of these volumes represent the relative selectivity of para-cresol with respect to meta-cresol.

Reproducible data from this test gave a relative para-cresol to meta-cresol selectivity of 1.53 which demonstrates the characteristic of the adsorbent which makes the adsorptive separation process possible.

EXAMPLE II

In this example three pulse tests A, B, and C were performed; tests A and B with the adsorbent described above and used for Example I and test C with an adsorbent comprising a type X zeolite having calcium at the exchangeable cationic sites. The results are shown in Table No. 3 below.

Table 3

| Test | Adsorbent | Desorbent Material | Selectivity, (B) p-Cresol/m-Cresol | p-Cresol Peak Envelope Width at Half Height, cc of desorbent material |
|---|---|---|---|---|
| | | Pulse Test Data for p-Cresol Separation | | |
| A | K-Ba-Type X | 30% phenol in Toluene | 1.37 | 17.0 |
| B | K-Ba-Type X | 50% hexanol-1 in Toluene | 1.8 | 11.0 |
| C | Ca-Type X | 50% hexanol-1 in Toluene | 0.92 | 8.0 |

The test procedure and equipment used was the same as that described in Example I.

For test A the desorbent material was 30 vol. % phenol in toluene and the feed mixture contained 5 vol. % each of para-cresol and meta-cresol in desorbent material. The relative selectivity of the adsorbent for para-cresol with respect to meta-cresol in the presence of this desorbent material was 1.37 and the para-cresol peak envelope width at half height was 17.0.

The same adsorbent was employed for test B but the desorbent material was 50 vol. % hexanol in toluene. Now the relative selectivity of the same adsorbent for para-cresol with respect to meta-cresol in the presence of this desorbent material was 1.8 or an increase of 31% over that of test A. The para-cresol peak envelope width at half height had decreased from 17.0 obtained for test A to 11.0 for test B indicating a faster rate of desorption of para-cresol for test B. The comparison of the results of test A and B, therefore indicates the improvements in the adsorbent characteristics of selectivity and transfer rate and hence in the separation process itself when a desorbent material comprising an alcohol is employed.

Test C was conducted with the same desorbent material as was used for test B but a different adsorbent was employed. The adsorbent used comprised a type X zeolite containing calcium cations at the exchangeable cationic sites. With the same desorbent material, hexanol-1 in toluene, this adsorbent exhibited essentially no selectivity for either cresol isomers thus indicating that this adsorbent, while suitable for use in the prior art cresol separation process, is not suitable for use in the cresol isomer separation process of this invention.

We claim as our invention:

1. A process for separating para-cresol from a feed mixture containing para-cresol and at least one other cresol isomer which process comprises the steps of:
   a. contacting, at adsorption conditions including a temperature of from about 100° F. to about 500° F. and a pressure of from about atmospheric to about 500 psig., said feed mixture with an adsorbent comprising a crystalline aluminosilicate selected from the group consisting of X structured and Y structured zeolites containing at the exchangeable cationic sites one or more selected cations, thereby selectively adsorbing para-cresol;
   b. withdrawing from the adsorbent a raffinate stream comprising less selectively adsorbed cresol isomers;
   c. thereafter contacting said adsorbent at adsorption conditions including a temperature of from about 100° F. to about 500° F. and a pressure from about atmospheric to about 500 psig. with a desorbent material comprising a saturated alcohol of from 1 to 7 carbon atoms per molecule and which is soluble in the feed mixture at said adsorption and desorption conditions and differing by at least about 15° F. in average boiling point from the feed mixture, whereby to remove adsorbed para-cresol from the adsorbent and to increase the selectivity of the adsorbent for para-cresol in subsequent contact of the feed mixture with the adsorbent;
   d. withdrawing from the adsorbent an extract stream containing desorbed para-cresol; and
   e. contacting an additional quantity of said feed mixture with the resultant adsorbent of increased selectivity for para-cresol.

2. The process of claim 1 further characterized in that said crystalline aluminosilicate is a X structured zeolite.

3. The process of claim 1 further characterized in that said crystalline aluminosilicate is a Y structured zeolite.

4. The process of claim 1 further characterized in that said crystalline aluminosilicate contains from about 4 to about 8 wt. % water on a volatile-free basis.

5. The process of claim 1 further characterized in that said cation is selected from the group consisting of Group IA, Group IIA, and Group IB metals of the Periodic Table of Elements.

6. The process of claim 1 further characterized in that said alcohol has a boiling point which is at least 15°F. less than that of the feed mixture.

7. The process of claim 1 further characterized in that said desorbent material comprises a mixture of said alcohol and a saturated or aromatic hydrocarbon which is soluble in both the feed mixture and the alcohol at both adsorption and desorption conditions and which has an average boiling point of substantially different than that of the feed mixture.

8. The process of claim 7 further characterized in that said hydrocarbon is a paraffin or a cycloparaffin.

9. The process of claim 7 further characterized in that said hydrocarbon is an aromatic.

10. The process of claim 9 further characterized in that said aromatic hydrocarbon is selected from the group consisting of benzene, toluene, and xylene.

11. The process of claim 7 further characterized in that said mixture contains from about 25 to about 75 vol. percent alcohol with said hydrocarbon.

12. The process of claim 5 further characterized in that said alcohol is a primary alcohol.

13. The process of claim 12 further characterized in that said crystalline aluminosilicate is a X structured zeolite.

14. The process of claim 12 further characterized in that said crystalline aluminosilicate is a Y structured zeolite.

15. The process of claim 12 further characterized in that said crystalline aluminosilicate contains from about 4 to about 8 wt. % water on a volatile-free basis.

16. The process of claim 13 further characterized in that said X structured zeolite contains barium and potassium at the exchangeable cationic sites.

17. The process of claim 13 further characterized in that said X structured zeolite contains barium at the exchangeable cationic sites within said zeolite.

18. The process of claim 14 further characterized in that said Y structured zeolite contains potassium at the exchangeable cationic sites.

19. The process of claim 12 further characterized in that said desorbent material contains said primary alcohol in admixture with a saturated or aromatic hydrocarbon which is soluble in both the feed mixture and the primary alcohol at adsorption and desorption conditions and which has an average boiling point substantially different than that of the feed mixture.

20. The process of claim 19 further characterized in that said hydrocarbon is a paraffin or cycloparaffin.

21. The process of claim 19 further characterized in that said hydrocarbon is an aromatic selected from the group consisting of benzene, toluene, and xylene.

22. The process of claim 19 further characterized in that said mixture contains from about 25 to about 75 vol. % primary alcohol with said hydrocarbon.

23. The process of claim 21 further characterized in that said primary alcohol is 1-hexanol.

24. The process of claim 21 further characterized in that said aromatic is toluene.

25. The process of claim 1 further characterized in that said alcohol is 1-hexanol.

* * * * *